United States Patent [19]
Lang et al.

[11] Patent Number: 5,637,295
[45] Date of Patent: Jun. 10, 1997

[54] METHODS AND COMPOSITIONS FOR PERMANENT SHAPING OF HAIR

[75] Inventors: Guenther Lang, Reinheim; Kirstin Uhl, Darmstadt; Gerhard Sendelbach, Darmstadt; Gerhard Maresch, Darmstadt, all of Germany

[73] Assignee: Wella Aktiengesellschaft, Darmstadt, Germany

[21] Appl. No.: 559,375

[22] Filed: Nov. 16, 1995

[30] Foreign Application Priority Data

Dec. 3, 1994 [DE] Germany ............ 44 43 062.0

[51] Int. Cl.$^6$ .................................................. A61K 7/09
[52] U.S. Cl. .................. 424/70.2; 424/70.5; 424/70.51; 424/70.12
[58] Field of Search ................ 424/70.2, 70.5, 424/70.51, 70.12

[56] References Cited

U.S. PATENT DOCUMENTS

| | | | |
|---|---|---|---|
| 4,891,166 | 1/1990 | Schafer et al. | 260/404.5 |
| 5,271,926 | 12/1993 | Kure et al. | 424/71 |
| 5,340,367 | 8/1994 | Schultz et al. | 8/432 |

FOREIGN PATENT DOCUMENTS

| | | |
|---|---|---|
| 0530974A1 | 3/1993 | European Pat. Off. . |
| 3719086C1 | 10/1988 | Germany . |
| 2197352A | 5/1988 | United Kingdom . |
| WO94/08556 | 4/1994 | WIPO . |
| WO94/21224 | 9/1994 | WIPO . |

OTHER PUBLICATIONS

Zeitschrift fur die Fett—. . . /Sacklofski, H./#17, Oct. 1989.

*Primary Examiner*—Margaret W. Glass
*Attorney, Agent, or Firm*—Michael J. Striker

[57] ABSTRACT

The permanent shaping composition for permanent shaping of hair includes from 2 to 25 percent by weight of a conventional keratin-reducing compound and from 0.02 to 5 percent by weight of certain diquaternary polysiloxanes. The permanent wave-pretreatment composition includes from 0.02 to 5 percent by weight of the diquaternary polysiloxanes. The permanent shaping composition advantageously includes mercaptocarbonic acid reducing agents and has a pH of from 6 to 10 and may include conventional cosmetic additives. Methods for using the permanent shaping composition and the permanent wave-pretreatment composition are described which provide a more uniform permanant wave from the hair roots to the hair tips.

6 Claims, 2 Drawing Sheets

METHODS AND COMPOSITIONS FOR PERMANENT SHAPING OF HAIR

BACKGROUND OF THE INVENTION

The invention described herein relates to a permanent wave pre-treatment composition and a permanent hair shaping composition containing a diquaternary polysiloxane as well as to a method for permanent shaping of hair using these compositions.

Hairs differ in their morphological structure from hair roots to hair tips. This is because, among other things, of the effect of the environment (e.g. the action of the sun or weathering factors) and of chemical and mechanical treatments of the hair (e.g. combing or brushing, permanent wave or dyeing treatments, washing) on the hair over the course of a lifetime. These external influences and the accompanying morphological changes of the hair cause an increased static charge on the hair, a poorer combability, a rough and unpleasant feel, a reduced gloss and an increased brittleness of the hair and, in extreme cases, can lead to breakage of the hairs during or after a permanent shaping treatment.

Many attempts have been made to solve these problems. For example the use of permanent shaping agents based on thioglycolic acid esters in the acidic to neutral pH range is recommended. Of course a comparatively uniform and safe shaping of hair from the hair roots to the hair tips is attained using the permanent shaping agents based on thioglycolic acid esters, however the physiological and particularly the sensitizing properties of thioglycolic acid ester are not satisfactory so that the use of other physiologically better reducing agents instead of thioglycolic acid ester is desirable. Similarly addition of cationic polymers and/or cationic surfactants to permanent shaping compositions is recommended in the Literature so that a good combability of the hair and a pleasant feel are obtained. However it has been shown that a nonuniform shaping of hair (comparatively strong shaping in the vicinity of the hair tips but comparatively weak shaping in the vicinity of the hair roots) is obtained using these agents for permanent shaping of hair.

SUMMARY OF THE INVENTION

It is an object of the present invention to provide a permanent hair shaping method and permanent shaping composition suitable for use in this method by which a safe and uniform permanent shaping of hair from the hair roots to the hair tips is possible while simultaneously providing good physiological compatibility, especially in regard to the sensitization risk.

Surprisingly it has been found that the aforesaid object of the invention is attained in an outstanding manner using a permanent shaping composition and/or permanent wave pre-treatment composition including diquaternary polysiloxanes.

According to the invention a permanent shaping composition for the permanent shaping of hair based on a keratin-reducing compound includes a diquaternary polysiloxane of the following formula (I):

$$\left[ Z-M-\underset{CH_3}{\underset{|}{\overset{CH_3}{\overset{|}{Si}}}}O-\left[\underset{CH_3}{\underset{|}{\overset{CH_3}{\overset{|}{Si}}}}O\right]_n-\underset{CH_3}{\underset{|}{\overset{CH_3}{\overset{|}{Si}}}}-M-Z \right]^{2+} 2X^-, \quad (I)$$

wherein Z is the group $$-\underset{R^3}{\overset{R^1}{\underset{|}{\overset{|}{N^+}}}}-R^2; \quad -\underset{R^5}{\overset{R^4}{\underset{|}{\overset{|}{N^+}}}}-(CH_2)_xR^6-\overset{O}{\overset{\|}{C}}R^7$$

or $$-\overset{R^9}{\underset{|}{N^+}}\underset{\underbrace{\phantom{xxxx}}}{\phantom{x}}\overset{\phantom{x}}{C}-R^{10}$$
(with =N in ring)

and $R^1$, $R^2$ and $R^3$ are each independently an alkyl group having from 1 to 22 carbon atoms, a hydroxyalkyl group having from 1 to 22 carbon atoms, an alkenyl group having from 2 to 22 carbon atoms or a hydroxyalkenyl group having from 2 to 22 carbon atoms, with the proviso that at least one of the $R^1$, $R^2$ and $R^3$ groups have at least ten carbon atoms; and $R^4$, $R^5$, $R^7$, $R^9$, $R^{10}$ are each independently an alkyl group having from 1 to 22 carbon atoms, a hydroxyalkyl group having from 1 to 22 carbon atoms, an alkenyl group having from 2 to 22 carbon atoms or a hydroxyalkenyl group having from 2 to 22 carbon atoms;

$R^6$=—O— or an —$NR^8$— group, wherein $R^8$ is an alkyl or hydroxyalkyl group having from 1 to 4 carbon atoms or a H group; and x=2 to 4;

wherein M is a divalent residue select from the following group:

| | |
|---|---|
| $-(CH_2)_3OCH_2CH(OH)CH_2-$ | $-(CH_2)_3OCH_2CH(CH_2OH)-$ |
| $-(CH_2)_2-CH(OH)-CH_2-$ | $-(CH_2)_2-CH-CH_2-OH$ (branched) |
| $-(CH_2)_3-CH(OH)-CH_2-$ | $-(CH_2)_3-CH-CH_2-OH$ (branched) |
| $-CH_2CH(CH_3)-$ cyclohexyl with OH and $CH_3$ substituents | $-CH_2CH(CH_3)-$ cyclohexyl with $CH_3$ and OH substituents |
| $-(CH_2)_2-$ cyclohexyl-OH | $-(CH_2)_2-$ cyclohexyl-OH |
| norbornyl-OH | norbornyl-OH | wherein the N atom of the Z group is connected with the M group at the carbon atom adjacent to the C—OH residue in the M group;

n=a number from 0 to 200;

and $X^-$ is an organic or inorganic anion, which originates from a common physiologically compatible acid, HX.

The diquaternary polysiloxane compounds of formula (I) which are particularly preferred are those in which:

M=—$(CH_2)_3OCH_2CH(OH)CH_2$—, Z=—$N^+R^4R^5$—$(CH_2)_xR^6$—CO—$R^7$;

$R^4$, $R^5$=—$CH_3$; $R^6$=—NH—; $R^7$=a coconut oil fatty acid group;

x=3; n=10 or 30 and X⁻=acetate anion.

The composition of the permanent shaping agent according to the invention corresponds to that for the known types of preparation based on a keratin-reducing compound.

The diquaternary polysiloxane of formula (I) is contained in this permanent shaping composition advantageously in an amount of from 0.02 to 5 percent by weight (in relation to the total amount of this ready-to-use preparation). An amount of from 0.05 to 5 percent by weight of the diquaternary polysiloxane is however particularly preferred in the permanent shaping composition according to the invention.

The permanent shaping composition according to the invention can be used in a number of types of preparations, of which only a few are exemplified in detail in the following.

The compositions for permanent shaping of hair according to the invention include weakly acidic to alkaline aqueous preparations having pH from 6 to 10 which contain a keratin-reducing compound, e.g. mercaptocarboxylic acids such as thioglycolic acid and thiolactic acid or their salts and 2-hydroxy-3-mercaptopropionic acid or its salts, cysteine or its salts; cysteamine or its salts and derivatives and sulfurous acid or its salts, alone or in combination with each other. The concentration of the keratin-reducing compound should amount to about 2 to 25% by weight, advantageously 5 to 18 percent by weight. The required pH value is adjusted by controlled addition of ammonia and organic amines as well as ammonium and alkali metal carbonates or hydrogen carbonates.

The composition for permanent shaping of hair can be in the form of an aqueous solution or emulsion, and in thickened form on an aqueous basis, especially a gel, cream or paste.

Understandably the permanent shaping composition can include known common cosmetic additives for compositions of this type, e.g. thickening agents, such as kaolin, bentonite, fatty acids, higher fatty alcohols, starch, polyacrylic acid and its derivatives, cellulose derivatives, alginate, vaseline or paraffin oils; wetting agents or emulsifiers from the classes of anionic, cationic, amphoteric or nonionic surfactant substances, e.g. fatty alcohol sulfates, fatty alcohol ether sulfates, alkyl sulfonates, alkyl benzene sulfates, quaternary ammonium salts, alkyl betaines, ethoxylated fatty acid esters; turbidity-inducing agents such as polyethyleneglycol ester, alcohols such as ethanol, propanol, isopropanol or glycerin, solvating agents; stabilizers; buffer substances; perfume oils, dyes and hair conditioning and hair care ingredients, such as lanolin derivatives, cholesterol, pantothenic acids or betaine. The above-mentioned components are used in amounts commonly used for their purposes, e.g. the wetting agents and emulsifiers can be contained in a concentration of 0.2 to 30 percent by weight, while the thickening agents can be contained in amounts of from 0.5 to 20 percent by weight in the hair shaping composition according to the invention.

Furthermore the so-called swelling and penetrating agents, such as dipropyleneglycolmonomethyl ether, 2-pyrrolidone or imidazolidin-2-one, can be added to the hair shaping composition according to the invention in amounts of from 0.5 to 20 percent by weight and dithiocompounds, e.g. dithiodiglycol acid, dithiodilactic acid or their salts can be added to prevent overcurling of the hair.

By variation of the pH a hair shaping composition can be provided, which is universally suitable for any type of hair structure, with addition of heat if necessarily to perform the permanent shaping of the hair. The composition provides a resilient, permanent and uniform shaping of the hair from the hair roots to the hair tips without causing allergic or sensitizing reactions. Particularly the hair shaping in the region of the hair roots is improved and an overcurling of the hair tips in comparison to the hair roots can be avoided. Furthermore the combability and shine or luster of the hair is improved.

The present invention also includes a process for permanent shaping of hair in which the hair is brought into a desired predetermined shape; the hair is treated with a permanent shaping composition prior to and/or after bringing it into the desired shape; the hair is rinsed with water; then subjected to an oxidative-after treatment, rinsed with water, put in a water wave if necessary and then dried. This process is distinguished from the prior art permanent shaping methods by using the permanent shaping composition according to the invention as the permanent shaping composition.

According to the process of the invention the hair can be washed with a shampoo and after that rinsed with water. Subsequently the hand towel-dried hair is divided into individual strands and wound on curlers with a diameter of 5 to 30 millimeters, advantageously from 5 to 15 millimeters. Then the hair is treated with a sufficient amount of the permanent shaping composition according to the invention for the hair shaping, advantageously from 60 to 120 grams.

After remaining on the hair for an acting time sufficient for permanent shaping of the hair, which, according to the properties of the hair, the pH, the shaping effectiveness of the permanent shaping composition and the application temperature, amounts to from 5 to 30 minutes (10 to 30 minutes without heating; 5 to 20 minutes with heating) the hair is rinsed with water and then oxidatively after-treated (i.e. "fixed"). The after treatment agent, is, applied in an amount determined by the amount of hair being treated, advantageously in an amount of from 80 to 100 grams.

For the oxidative after-treatment each after-treatment agent known up to now to be suitable can be used. For example, oxidizing agents used in this type of oxidative after-treatment agent include potassium and sodium bromate, sodium perborate, urea peroxide and hydrogen peroxide. The concentration of the oxidizing agent differs according to the application time (usually about 5 to 15 minutes) and the application temperature. The oxidizing agent is normally present in the ready-to-use aqueous after-treatment composition in a concentration of from 0.5 to 10 percent by weight. The agent for oxidative after-treatment can understandably include additional substance, such as wetting agents, hair care materials such as cationic polymers, weak acids, buffer substances or peroxide stabilizers and can be in the form of an aqueous solution, an emulsion and in thickened form on an aqueous basis, particularly as a cream, gel or paste.

Subsequently the curlers are removed. As needed, the unwound hair can be again subjected to an oxidative after-treatment. Then the hair is rinsed with water, put in a water wave if necessary and finally dried.

The subject matter of the invention also includes a pre-treatment composition for use in a method of permanent shaping of hair. This pre-treatment composition is called a permanent wave pre-treatment composition herein. The permanent wave pre-treatment composition according to the invention comprises a diquaternary polysiloxane of the above-described formula (I). However a permanent wave pre-treatment composition containing the diquaternary polysiloxanes of formula I in which $M=-(CH_2)_3OCH_2CH(OH)CH_2-$, $Z=-N^+R^4R^5-(CH_2)_xR^6-CO-R^7$;

$R^4$, $R^5$=—$CH_3$; $R^6$=—NH—; $R^7$=a coconut oil fatty acid group;

x=3; n=10 or 30 and $X^-$=acetate anion is particularly preferred.

The permanent wave pre-treatment composition according to the invention is free of reducing agents and can be in the form of an aqueous solution or emulsion and also in thickened form on an aqueous basis, particularly as a gel or cream.

Understandably the permanent wave pre-treatment composition can include known common cosmetic additives for compositions of this type, e.g. thickening agents, such as fatty acids, higher fatty alcohols, polyacrylic acid and its derivatives, cellulose derivatives, alginate, vaseline or paraffin oils; wetting agents or emulsifiers from the classes of cationic, amphoteric or nonionic surfactant substances, e.g. quaternary ammonium salts such as cetyltrimethylammonium chloride, cetyltribenzyl-dimethylammonium chloride, decyldimethyloctylammonium chloride, cetylpyridinium chloride, ethoxylated alkylammonium phosphates, coconut oil-pentaethoxymethylammonium methosulfate or caster oil fatty acid amidopropyltrimethylammonium methosulfate, alkylbetaines, amphoteric imidazole derivates or ethoxylated alkylphenols; turbidity-inducing agents such as polyethyleneglycol ester; alcohols such as ethanol, propanol, isopropanol or glycerin; solvating agents; silicone oils; stabilizers; perfume oils; natural materials; antioxidants; complex formers; buffer substances; dyes; and hair conditioning and hair care ingredients, such as lanolin derivatives, cholesterol, pantothenic acids or betaine. The above-mentioned components are used in amounts commonly used in permanent wave pre-treatment compositions, e.g. the perfume oils in an amount of from 0.1 to 5 percent by weight, the dyes in an amount of from 0.05 to 2 percent by weight, the thickeners in an amount of from 0.5 to 10 percent by weight and the wetting agents and emulsifiers can be present up to a maximum of 2% by weight, but are preferably present in a total concentration of 0.02 to 30 percent by weight.

The permanent wave pre-treatment composition is advantageously free of anionic emulsifiers and wetting agents.

An improved structure equalization occurs between the hair roots and hair tips as a result of the treatment of the hair with this permanent wave pre-treatment composition prior to performing the permanent shaping of the hair. Because of that a uniform shaping of the hair is possible.

An additional part of the present invention is a method of performing a permanent shaping of hair in which the hair is treated with a permanent wave pre-treatment composition prior to winding the hair on curlers, after the pre-treatment the hair is wound on curlers and is treated with a permanent shaping composition; then the hair is rinsed with water; then the hair is subjected to an oxidative-after treatment, rinsed with water, put in a water wave if necessary and thereafter dried. This process is distinguished from prior art permanent shaping methods which utilize a permanent wave pre-treatment composition by use of the pre-treatment composition according to the invention containing the diquaternary polysiloxanes of formula (I) as the pre-treatment composition.

In an additional embodiment of this process the above-described diquaternary polysiloxanes of formula (I) are included in the permanent shaping composition as well as in the permanent wave pre-treatment composition according to the invention.

According to the process of the invention the hair is moistened with the permanent wave pre-treatment composition prior to being wound on the curlers, if necessary rubbed with a hand towel, divided into individual strands and wound on curlers with a diameter of 5 to 30 millimeters, advantageously from 5 to 15 millimeters. If necessary the hair can be washed with a shampoo prior to the treatment with the permanent wave pre-treatment composition and subsequently rubbed with a hand towel.

Then the hair is treated with a sufficient amount of the permanent shaping composition according to the invention for the hair shaping, advantageously from 60 to 120 grams.

After remaining on the hair for an acting time sufficient for permanent shaping of the hair, which, according to the properties of the hair, the pH, the shaping effectiveness of the permanent shaping composition and the application temperature, amounts to from 5 to 30 minutes (10 to 30 minutes without heating; 5 to 20 minutes with heating) the hair is rinsed with water and then oxidatively after-treated (i.e. "fixed"). The after treatment agent, is, applied in an amount determined by the amount of hair being treated, advantageously an amount of from 80 to 100 grams.

For the oxidative after-treatment each after-treatment agent known up to now to be suitable can be used. For example, oxidizing agents used in this type of oxidative after-treatment agent include potassium and sodium bromate, sodium perborate, urea peroxide and hydrogen peroxide. The concentration of the oxidizing agent differs according to the application time (usually about 5 to 15 minutes) and the application temperature. The oxidizing agent is normally present in the ready-to-use aqueous after-treatment composition in a concentration of from 0.5 to 10 percent by weight. The agent for oxidative after-treatment can understandably include additional substance, such as wetting agents, hair care materials such as cationic polymers, weak acids, buffer substances or peroxide stabilizers and can be in the form of an aqueous solution, an emulsion and in thickened from on an aqueous basis, particularly as a cream, gel or paste.

Subsequently the curlers are removed. As needed, the unwound hair can be again subjected to an oxidative after-treatment. Then the hair is rinsed with water, put in a water wave if necessary and finally dried.

A safe and uniform shaping of the hair from the hair roots to the hair tips is attained by the above-described process.

The following examples illustrate the invention in greater detail however they should not be construed as further limiting the scope of the appended claims.

EXAMPLES

Example 1: Two Component-Permanent Wave Pre-treatment Composition

| Component 1: | |
|---|---|
| 96.398 g | isoparaffin |
| 2.400 g | isopropanol |
| 1.200 g | perfume oil |
| 0.002 g | dye |
| 100.0 g | |
| Component 2: | |
| 0.250 g | cetyltrimethylammonium chloride |
| 0.250 g | cocobetaine |
| 1.000 g | diquaternary polysiloxane of formula (I) (Tradename: ABIL® QUAT 3270 of Th. Goldschmidt AG, Essen/Germany) |
| 0.004 g | Dye |
| 98.496 g | Water |
| 100.0 g | |

Components 1 and 2 are mixed with each other in a weight ratio of 3:4 immediately prior to application. The ready-to-use permanent wave pre-treatment composition so obtained is applied to hand towel-dried normal undamaged hair in connection with a hair washing process. The hair is then rubbed with a hand towel, divided into strands and wound on curlers with a diameter of 6 millimeters. Subsequently a common permanent shaping composition (12.25% by weight ammonium thioglycolate; pH=8.1) containing no hair care materials is applied to the hair wound on the curlers. After an acting time of 18 minutes the hair is rinsed with water and subjected to an oxidative after-treatment ("fixed") with a 3% by weight aqueous hydrogen peroxide solution, rinsed anew with water, set in a hair-do and dried.

The result of the permanent shaping treatment with the above exemplary compositions is a uniform shaping of the hair from the hair roots to the hair tips.

Example 2: Permanent Shaping Composition for Normal Hair

| | |
|---|---|
| 11.9 g | ammonium thioglycolate |
| 5.0 g | ammonium hydrogen carbonate |
| 1.0 g | lauryl alcohol ethoxylated with 4 Mol ethylene oxide |
| 0.5 g | ammonia (25% aqueous solution) |
| 0.5 g | cocoamidopropylbetaine |
| 0.5 g | perfume oil |
| 2.0 g | diquaternary polysiloxane of formula (I) (Tradename: ABIL ® QUAT 3270 of Th. Goldschmidt AG, Essen, Germany) |
| 0.1 g | vinylpyrrolidone/styrene mixed polymerizate (Tradename: ANTARA ® 430 of the GAF Corp., New York, USA) |
| 78.5 g | water |
| 100.0 g | |

The pH of this permanent shaping composition amounts to 8.3. Normal, undamaged hair is washed, rubbed with a hand towel and then wound on curlers with a diameter of 6 millimeters. Subsequently the hair is moistened uniformly with the above-described permanent shaping composition and after an acting time of 18 minutes rinsed thoroughly with water at room temperature. Then the hair is subjected to an oxidative after-treatment with 80 grams of a 3 percent by weight hydrogen peroxide solution, rinsed again with water, put in a water wave and dried. The hair so treated has a very uniform and vivacious curl.

Example 3: Permanent Shaping Composition for Normal Hair and Difficult-to-shape Hair

| | |
|---|---|
| 14.2 g | ammonium thioglycolate |
| 5.5 g | ammonium hydrogen carbonate |
| 3.0 g | 1,2-propandiol |
| 1.2 g | castor oil ethoxylated with 40 Mol ethylene oxide |
| 1.0 g | ammonia (25% aqueous solution) |
| 0.8 g | perfume oil |
| 0.5 g | poly(dimethyldiallylammonium chloride) |
| 0.3 g | vinylpyrrolidone/styrene mixed polymerizate (Tradename: ANTARA ® 430 of the GAF Corp., New York, USA) |
| 1.0 g | diquaternary polysiloxane of formula (I) (Tradename: ABIL ® QUAT 3270 of Th. Goldschmidt AG, Essen, Germany) |
| 72.5 g | water |
| 100.0 g | |

The pH of this composition amounts to 8.5.

This permanent shaping composition is applied to the hair in the same way as the composition described in Example 2, except that the acting time of the permanent shaping composition amounts to 20 minutes.

A naturally acting, uniform shaping of hair from the hair roots to the hair tips is obtained using this composition.

Example 4: Permanent Shaping Composition for Dyed Hair

| | |
|---|---|
| 9.1 g | ammonium thioglycolate |
| 2.5 g | ammonium hydrogen carbonate |
| 1.0 g | castor oil ethoxylated with 40 Mol ethylene oxide |
| 1.0 g | poly(dimethyldiallylammonium chloride) |
| 1.0 g | cocobetaine |
| 0.6 g | perfume oil |
| 0.4 g | ammonia (25% aqueous solution) |
| 3.0 g | diquaternary polysiloxane of formula (I) (Tradename: ABIL ® QUAT 3270 of Th. Goldschmidt AG, Essen, Germany) |
| 81.4 g | water |
| 100.0 g | |

The pH of this composition amounts to 8.0.

The hair damaged by the hair dyeing process is washed with a mild shampoo, dried with a hand towel and wound on curlers with a diameter of 8 millimeters. Subsequently the above-described permanent shaping composition is distributed uniformly on the wound hair. After an acting time of 15 minutes the wound hair is rinsed with water and dried gently with a hand towel. Then the wound hair is subjected to an oxidative after-treatment with a 2.5-percent aqueous hydrogen peroxide solution. After an acting time of 5 minutes the curlers are removed, the hair rinsed with water, then rubbed with a hand towel set or put in a hair-do and dried.

A uniform, resilient permanent shaping of hair results using the above composition.

Example 5: Permanent Shaping Composition for Dyed Hair

| | |
|---|---|
| 12.0 g | cysteine hydrochloride |
| 4.2 g | amonium thioglycolate |
| 6.0 g | ammonia (25% aqueous solution) |
| 3.0 g | 1,2-propandiol |
| 3.0 g | 1,2-butandiol |
| 3.0 g | copolymer of vinylpyrrolidone and dimethylaminoethylmethacrylate, quaternarized with diethyl sulfate (20% aqueous solution, Tradename: GAQUAT ® 755 of GAF Corp., New York, USA) |
| 2.0 g | ammonium hydrogen carbonate |
| 0.8 g | cocoamidopropylbetaine |
| 2.0 g | diquaternary polysiloxane of formula (I) (Tradenamle: ABIL ® QUAT 3270 of Th. Goldschmidt AG, Essen, Germany) |
| 0.1 g | vinylpyrrolidone/styrene mixed polymerizate (Tradename: ANTARA ® 430 of the GAF Corp., New York, USA) |
| 63.9 g | water |
| 100.0 g | |

The pH of this permanent shaping composition amounts to 8.2.

The hair is treated in the manner described in Example 4 except that the acting time of the permanent shaping composition on the hair was 15 minutes.

The hair so treated had a uniform curliness with curls having good elasticity and springiness.

In the diquaternary polysiloxane of formula I (Tradename: ABIL®-QUAT 3270) used in Examples 1 to 5 $M=-(CH_2)_3OCH_2CH(OH)CH_2-$, $Z=-N^+R^4R^5-(CH_2)_xR^6-CO-R^7$;

$R^4$, $R^5=-CH_3$; $R^6=-NH-$; $R^7=$a coconut oil fatty acid group;

x=3; n=10 and $X^-=$acetate anion.

BRIEF DESCRIPTION OF THE DRAWING

The objects, features and advantages of the present invention will now be illustrated in more detail by the following comparative experiments, reference being made to the accompanying drawing in which.

Example 6: Comparative Experiments

Figure 1:
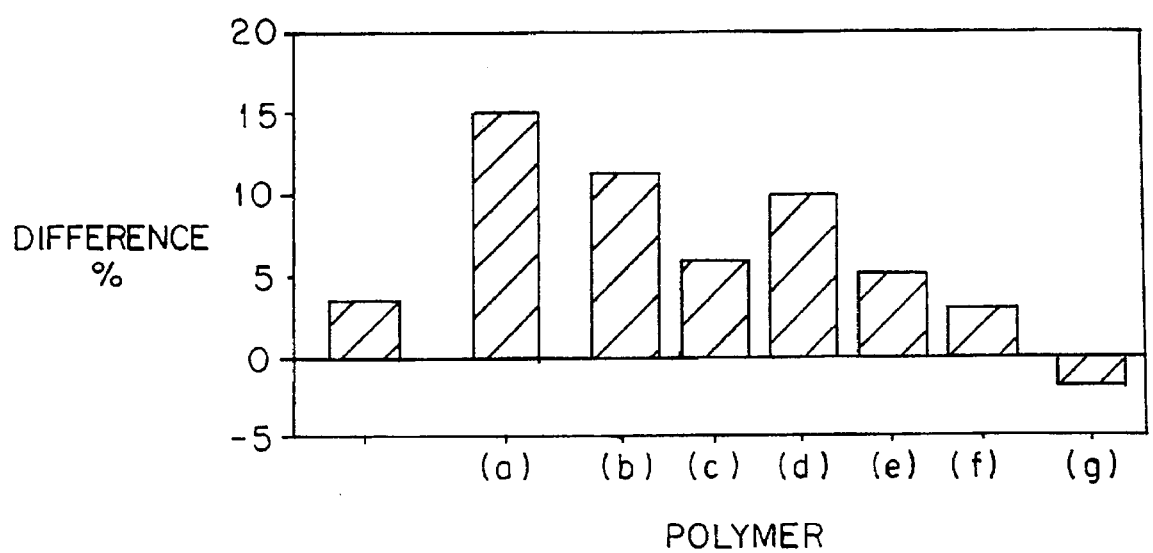
FIG. 1 is a graphical illustration showing the dependence of measured curl retention on the polymer present in the permanent shaping composition used to treat hair strands.

For the comparative experiments numerous hair strands each including 100 hairs of the same quality were wound on spiral-shaped curlers and treated in the usual way with a composition according to the invention. After an acting time of the permanent shaping composition of 10 minutes at 45° C. the hair was rinsed with water and then subjected to an oxidative after-treatment. After the drying the hair strands were wound on curlers and suspended in a warm water bath at 40° C.

Subsequently the total length of the hair strands and the length of the individual curl coils was measured after predetermined time intervals of 0, 10, 60, 120, 240 and 360 minutes. The total length of the hair strand was used to calculate the curl retention for each strand according to the following formula:

$$\text{Curl retention, } \% = 100 \cdot (l_o - l_t)/(l_o - l_1)$$

wherein $l_o$=length of stretched or straightened hair strand, $l_t$=length of suspended hair strand after t minutes, and $l_1$=length of the shaped, wound hair strand.

The wave stability or curl retention is a measure of the effectiveness of the permanent shaping composition and the retainability or hold of the permanent wave obtained from its use. The length of a curl coil is characterized in the following as the curl strength (in mm/curl). It is a good parameter for characterization of the curl form. A smaller value for the curl strength means a short-curled wave form.

The curl retention and the curl strength of the hair treated with a mildly alkaline permanent shaping composition of the following composition

| | |
|---|---|
| 11.9 g | ammonium thioglycolate |
| 5.0 g | ammonium hydrogen carbonate |
| 5.0 g | polymer (a) to (g) |
| 1.0 g | lauryl alcohol ethoxylated with 4 Mol ethylene oxide |
| 0.5 g | ammonia (25% aqueous solution) |
| 0.5 g | cocoamidopropylbetaine |
| 0.5 g | perfume oil |
| 75.6 g | water |
| 100.0 g | | were measured for both the hair roots and the hair tips.

The pH of this permanent shaping composition was 8.3. The polymers (a) to (g) used in it were as follows:

(a) polyquaternium-6 (poly(diallyldimethylammonium chloride))

(b) polyquaternium-16 (copolymer made from vinyl imidazoliummethochloride and vinylpyrrolidone)

(c) CROQUAT® WKP of Croda, Germany (quaternarized egg white hydrolyzate)

(d) Dow Corning® 929 Cationic Emulsion of Dow Corning Europe/Belgium (cationic emulsion made from amodimethicone, tallowtrimonium chloride, and nonoxynol-10)

(e) Pecosil SMQ-40 of Pheonix Chemical Inc./USA (dimethicone copolyol phospho myristyl ammonium chloride)

(f) Pecosil SWP Q 40 of Pheonix Chemical Inc./USA (quaternary egg white hydrolyzate/dimethicone copolyol phosphate)

(g) ABIL®-QUAT 3270 (diquaternary polysiloxane of formula (I))

The results for the measurement of curl retention after a suspension time of t=360 minutes for hair strands treated with the above-described permanent shaping compositions are summarized in the following Table I.

TABLE I

DEPENDENCE OF CURL RETENTION ON THE POLYMER PRESENT IN THE PERMANENT SHAPING COMPOSITION

| POLYMER vs. Roots, % | Curl Retention at Hair Roots, % | Curl Retention at Hair Tips, % | Difference in Curl Retention at Hair Tips |
|---|---|---|---|
| without polymer | 39.8 | 43.4 | 3.6 |
| (a) | 36.9 | 51.8 | 14.9 |
| (b) | 38.1 | 49.2 | 11.1 |
| (c) | 41.1 | 46.9 | 5.8 |
| (d) | 37.2 | 46.9 | 9.7 |
| (e) | 38.7 | 43.8 | 5.1 |
| (f) | 44.1 | 47.1 | 3.0 |
| (g) | 47.0 | 45.0 | -2.0 |

From Table I it is apparent that the difference between the curl retention at the hair roots and the hair tips is least when the permanent shaping composition according to the invention includes the polymer (g), and no "overcurling" is found to occur at the hair tips. In fact, the shaping of the hair in the vicinity of the hair roots is somewhat stronger than at the hair tips.

These results are also clearly shown in the bar graph in FIG. 1.

In contrast to the example of the permanent shaping composition according to the invention which includes polymer (g) the results for the prior art permanent shaping compositions show more or less large differences in curl retention at the hair tips and hair roots which are a particular problem with the composition containing polyquaternium-6, i.e. polymer (a). As a result of these differences in curl retention at the hair roots and hair tips a troublesome and nonuniform permanent shaping results when the permanent shaping compositions of the prior art are used, which are even, in some case, poorer than the results obtained with the permanent shaping composition which is completely free of polymer.

Besides the curl retention the curl strength provided another possiblity for a quantitative evaluation of the permanent shaping results in the vicinity of the hair roots and the hair tips. An overview of the results for curl strength are provided in the following Table II which shows the difference between the curl strength at the hair roots and at the hair tips.

TABLE II

DIFFERENCE IN CURL STRENGTH AT THE HAIR ROOTS AND HAIR TIPS ACCORDING TO THE POLYMER IN THE SHAPING COMPOSITION

| POLYMER | Difference in Curl Strength, mm |
|---|---|
| without polymer | 3.58 |
| (a) | 8.83 |
| (b) | 5.95 |

TABLE II-continued

| DIFFERENCE IN CURL STRENGTH AT THE HAIR ROOTS AND HAIR TIPS ACCORDING TO THE POLYMER IN THE SHAPING COMPOSITION | |
|---|---|
| POLYMER | Difference in Curl Strength, mm |
| (c) | 4.69 |
| (d) | 5.40 |
| (e) | 6.43 |
| (f) | 4.12 |
| (g) | 1.60 |

Figure 2:
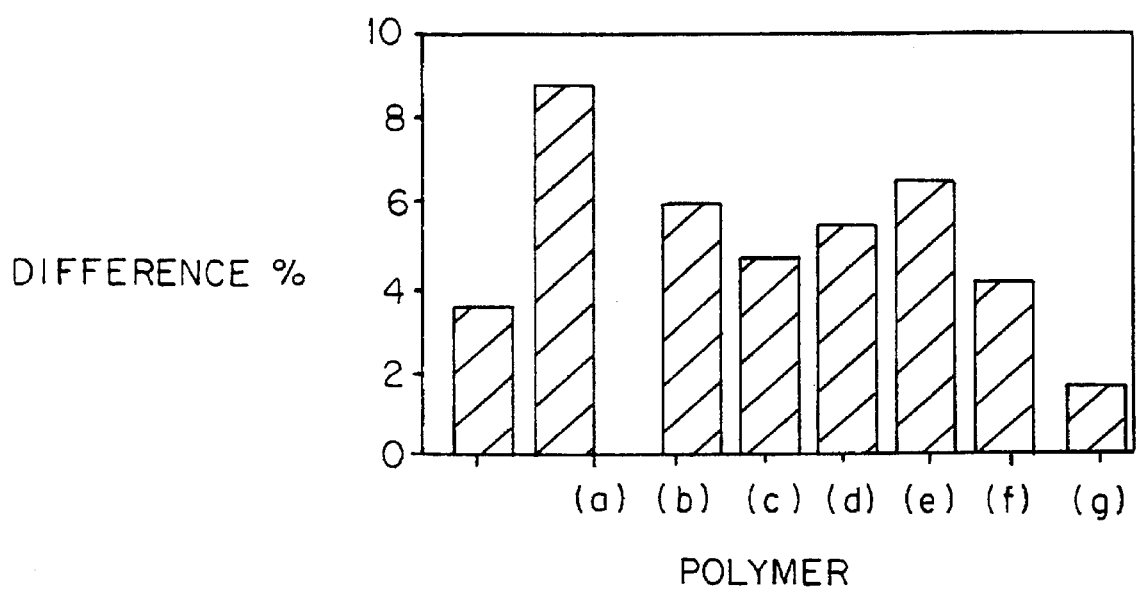
FIG. 2 is a graphical illustration showing the dependence of measured curl strength on the polymer present in the permanent shaping composition used to treat hair strands.

These results are illustdrated in FIG. 2.

Table II and FIG. 2 clearly show that the curl strength in the vicinity of the hair tips is significantly smaller than in the vicinity of the hair roots when the hair is treated with the permanent shaping composition according to the prior art which does not contain polymer (g). This means that the curl form is always shorter-curled from the hair roots to the hair tips. A curl form of this type is very troublesome and produces particularly a tendency to overcurl, particularly because of the shorter curled region at the hair tips.

In contrast the curl strength which is obtained when the hair shaping composition according to the invention including polymer (g) is used to treat the hair strands is nearly the same at the hair tips and at the hair roots. In this case a uniform curl form is obtained which provides a good permanent wave in the vicinity of the hair roots.

Unless otherwise indicated all percentages are percentages by weight.

While the invention has been illustrated and described as embodied in a method and composition for the permanent shaping of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A permanent shaping composition for permanent shaping of hair comprising a keratin-reducing compound and a diquaternary polysiloxane of the formula (I):

$$\left[ Z-M-\underset{\underset{CH_3}{|}}{\overset{\overset{CH_3}{|}}{Si}}O\left[\underset{\underset{CH_3}{|}}{\overset{\overset{CH_3}{|}}{Si}}O\right]_n\underset{\underset{CH_3}{|}}{\overset{\overset{CH_3}{|}}{Si}}-M-Z \right]^{2+} 2X^-, \quad (I)$$

wherein Z is the group

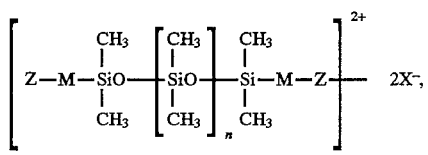

or

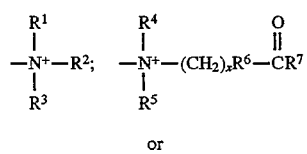

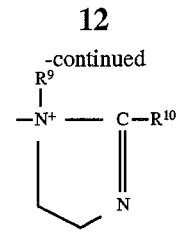

and $R^1$, $R^2$ and $R^3$ are each, independently, selected from the group consisting of alkyl groups having from 1 to 22 carbon atoms, hydroxyalkyl groups having from 1 to 22 carbon atoms, alkenyl groups having from 2 to 22 carbon atoms and hydroxyalkenyl groups having from 2 to 22 carbon atoms, with the proviso that at least one of the $R^1$, $R^2$ and $R^3$ groups have at least ten of said carbon atoms;

and $R^4$, $R^5$, $R^7$, $R^9$, $R^{10}$ are each, independently, selected from the group consisting of alkyl groups having from 1 to 22 carbon atoms, hydroxyalkyl groups having from 1 to 22 carbon atoms, alkenyl groups having from 2 to 22 carbon atoms and hydroxyalkenyl groups having from 2 to 22 carbon atoms;

$R^6$ is an —O— group or an —NR$^8$— group;

$R^8$ is selected from the group consisting of H, alkyl groups having from 1 to 4 carbon atoms and hydroxyalkyl groups having from 1 to 4 carbon atoms;

x=2 to 4; and wherein M is a divalent group selected from the group consisting of the following residues:

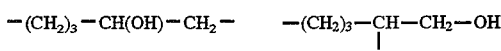
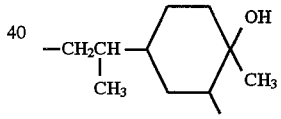 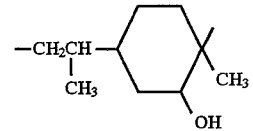
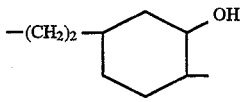 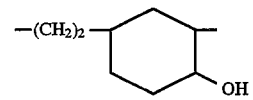
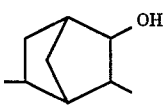 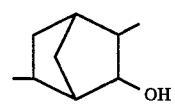

wherein the N atom of the Z group is connected with the M group at the carbon atom adjacent to the C—OH residue in the M group;

n=a number from 0 to 200, and X$^-$ is an organic or inorganic anion derived from a physiologically compatible acid, HX.

2. The permanent shaping composition as defined in claim 1, wherein the keratin-reducing compound is at least one member selected from the group consisting of thioglycolic acid, salts of thiolactic acid, 2-hydroxy-3-mercaptopropionic acid, salts of 2-hydroxy-3-mercaptopropionic acid, cysteine, salts of cysteine, cysteamine, salts of cysteamine, sulfurous acid and salts of sulfurous acid.

3. The permanent shaping composition as defined in claim 1, containing from 2 to 25 percent by weight of the keratin-reducing compound and from 0.02 to 5 percent by weight of said diquaternary polysiloxane.

4. The permanent shaping composition as defined in claim 1, wherein said diquaternary polysiloxane compounds said $M=-(CH_2)_3OCH_2CH(OH)CH_2-$, said $Z=-N^+R^4R^5-(CH_2)_xR^6-CO-R^7$; said $R^4$ and $R^5=-CH_3$; $R^6=-NH-$; said $R^7=$ a coconut oil fatty acid group; said $x=3$; said $n=10$ or 30 and said $X^-=$ acetate anion.

5. A method of permanent shaping of hair comprising the steps of:

a) bringing the hair into a predetermined shape;

b) treating the hair with a permanent shaping composition as defined in claim 1;

c) rinsing the hair with water;

d) subjecting the hair to an oxidative-after treatment; and e) rinsing the hair with water and drying the hair thereafter;

to provide a uniform shaping of the hair from hair roots of the hair to hair tips.

6. The method as defined in claim 5, further comprising putting the hair in a water wave after the subjecting of the hair to the oxidative after-treatment.

* * * * *